United States Patent [19]

Wojtowicz

[11] 3,988,336

[45] Oct. 26, 1976

[54] PREPARATION OF DIHALOISOCYANURIC ACID SALTS

[75] Inventor: John A. Wojtowicz, Cheshire, Conn.

[73] Assignee: Olin Corporation, New Haven, Conn.

[22] Filed: June 30, 1975

[21] Appl. No.: 591,579

[52] U.S. Cl. .......................................... 260/248 C
[51] Int. Cl.$^2$ ........................................ C07D 251/12
[58] Field of Search .............................. 260/248 C

[56] References Cited
UNITED STATES PATENTS
3,894,017  7/1975  Wojtowicz .......................... 260/248

Primary Examiner—John M. Ford
Attorney, Agent, or Firm—James B. Haglind; Donald F. Clements; Thomas P. O'Day

[57] ABSTRACT

Dihaloisocyanuric acid salts are produced in a process reacting a solid monometal cyanurate selected from the group consisting of a monoalkali metal cyanurate or a monoalkaline earth metal dicyanurate with a gaseous mixture of a dihalogen monoxide and an inert gas. The gaseous mixture is comprised of from about 1 to about 30 percent by volume of the dihalogen monoxide.

Alkali metal and alkaline earth metal dihaloisocyanurates and their hydrates are produced in the absence of a solvent as dry, free-flowing products.

12 Claims, No Drawings

PREPARATION OF DIHALOISOCYANURIC ACID SALTS

This invention relates to a process for the production of salts of dihaloisocyanuric acids. More particularly, this invention relates to a process for the production of alkali metal and alkaline earth metal dihaloisocyanurates. The salts are well known products used in laundry, bleaching and sanitizing applications.

It is known to produce alkali metal or alkaline earth metal chloroisocyanurates by chlorinating an alkali metal or alkaline earth metal cyanurate in an aqueous solution. For example, in U.S. Pat. No. 3,035,056, issued on May 15, 1962, to W. F. Symes and N. S. Hadzekyriakides, trisodium cyanurate is chlorinated at a temperature range of 0°–60° C. and a pH of 5.0 to 8.5. In U.S. Pat. No. 3,072,654, issued Jan. 8, 1963, to S. Vazopolos, an aqueous slurry of tricalcium diisocyanurate is chlorinated at a pH of from about 4.5 to 7.5 and a temperature range of from about 10°–65° C. The polychloroisocyanuric acid salts produced in these processes are only incompletely recovered as a portion remains dissolved in the aqueous medium. This soluble portion is recovered with difficulty or if not recovered, the waste solution must be properly treated. Either recovery of the chloroisocyanurate salts or disposal of the waste solutions involves considerable expense. Further, these processes produce as a by-product, an alkali metal or alkaline earth metal chloride which also requires removal and disposal.

In addition, in all of the above processes the polychloroisocyanurate is obtained as a wet product which must be dried to be sold commercially, or suitably used in many applications.

There is need therefore, of a process for the production of alkali metal and alkaline earth metal dihaloisocyanurates which does not require use of a liquid solvent medium and a separate drying step.

An object of the present invention is a novel process for producing alkali metal and alkaline earth metal dihaloisocyanurates in the absence of solvents.

Another object of the present invention is a process for producing alkali metal and alkaline earth metal dihaloisocyanurates which provides complete recovery of the products.

A further object of the present invention is a process in which a dihaloisocyanurate salt is obtained directly as a dry product.

These and other objects of the invention will be apparent from the following detailed description of the invention.

Briefly the process of the present invention for preparing a dihaloisocyanuric acid salt comprises reacting a gaseous mixture containing a dihalogen monoxide and an inert gas with a solid monoalkali metal cyanurate, or a monoalkaline earth metal dicyanurate. The gaseous mixture is comprised of from about 1 to about 30 percent by volume of the dihalogen monoxide.

Suitable dihalogen monoxides which can be used in the novel process of the present invention include dichlorine monoxide and dibromine monoxide, with dichlorine monoxide being preferred. These compounds are prepared by processes well known in the prior art, for example, by the reaction of the halogen gas with mercuric oxide according to the equation:

$$2X_2 + 2HgO \rightarrow X_2O + HgX_2 \cdot HgO \qquad (1)$$

wherein X is chlorine or bromine.

Another suitable method of preparation for dichlorine monoxide is the chlorination of sodium carbonate or sodium bicarbonate illustrated by the following equations:

$$2Cl_2 + 2Na_2CO_3 + H_2O \rightarrow Cl_2O + 2NaHCO_3 + 2NaCl \qquad (2)$$

$$2Cl_2 + 2NaHCO_3 \rightarrow Cl_2O + 2CO_2 + H_2O + 2NaCl \qquad (3)$$

A detailed procedure for each of these methods of preparation for dichlorine monoxide is given in the publication Inorganic Synthesis, 5, 156–160, (N.Y. McGraw-Hill, 1957). The preparation of dibromine monoxide is described in "Bromine and Its Compounds" edited by E. Jolles, (N.Y., Academic Press, 1966) pages 148–49.

To eliminate potential explosion hazards the dihalogen monoxide is employed in a gaseous mixture with a gas which is inert to the conditions of the reaction. Suitable inert gases include air, nitrogen, carbon dioxide, chlorine, and nitrous oxide, with air and nitrogen being preferred. The gaseous mixture suitably comprises from about 1 percent to about 30 percent by volume of dihalogen monoxide. Preferably, the gaseous mixture comprises from about 5 percent to about 25 percent and more preferably from about 10 percent to about 23 percent of dihalogen monoxide.

In the novel process of the present invention, the gaseous mixture is reacted with a solid monometal cyanurate such as a monoalkali metal cyanurate or monoalkaline earth metal dicyanurate. Suitable monoalkali metal cyanurates which may be employed, include monosodium cyanurate, monolithium cyanurate, monopotassium cyanurate, monorubidium cyanurate, and monocesium cyanurate, their hydrates and mixtures thereof. Monosodium cyanurate, monopotassium cyanurate, their hydrates and mixtures thereof are preferred embodiments, with monosodium cyanurate, monosodium cyanurate monohydrate and mixtures thereof being most preferred.

Monoalkaline earth metal dicyanurates which may be used, include monocalcium dicyanurate, monomagnesium dicyanurate, monobarium dicyanurate, and monostrontium dicyanurate, their hydrates and mixtures thereof. Monocalcium and monomagnesium dicyanurate, their hydrates and mixtures thereof are preferred embodiments.

The monometal cyanurates are prepared by known means, for example, by the reaction of stoichiometric proportions of cyanuric acid with a basic alkali metal or alkaline earth metal compound, such as the hydroxide, which yields the monometal cyanurate.

The reaction for preparing alkali metal haloisocyanurates, for example, sodium dihaloisocyanurate, is believed to proceed according to the following equation:

$$NaH_2C_3N_3O_3 + X_2O \rightarrow NaX_2C_3N_3O_3 \cdot H_2O \qquad (4)$$

The reaction using a monoalkaline earth metal, cyanurate, for example, monocalcium cyanurate is believed to proceed according to the following equation:

$$Ca(H_2C_3N_3O_3)_2 + 2X_2O \rightarrow Ca(X_2C_3N_3O_3)_2 \cdot 2H_2O \qquad (5)$$

The reaction is carried out at temperatures in the range of from about 0° C. to about 175° C. and preferably from about 20° C. to about 100° C. The reaction temperature is suitably selected to be substantially inversely related to the time of contact between the dihalogen monoxide gas and the solid monometal cyanurate in the reactor. A contact time between the gaseous mixture and the solid monometal cyanurate of from about 0.1 second to about 30 minutes may be suitably employed. A preferred contact time is from about 0.2 seconds to about 15 minutes and more preferably from about 0.5 seconds to about 4 minutes.

Any suitable proportions of monometal cyanurate and dihalogen monoxide may be used. For example, in reacting a monoalkali metal cyanurate, a molar ratio of dihalogen monoxide gas to the cyanurate of from about 0.6:1 to about 2:1 and preferably from about 0.8:1 to about 1.2:1 is employed. Where the monometal cyanurate is an alkaline earth metal dicyanurate, a molar ratio of dihalogen monoxide gas to the monoalkaline earth metal dicyanurate of from about 1.2:1 to about 4:1, and preferably from about 1.6:1 to about 2.4:1 is suitably employed.

The solid monometal cyanurate can be reacted as the anhydrous salt or, where existent, as the hydrate in either the granular or finely-divided form. Where a finely-divided monometal cyanurate is reacted, a suitable particle size distribution range is, for example, from about 2 to about 300 microns. A preferred particle size distribution for finely-divided monometal cyanurate is from about 10 to about 150 microns.

Water is formed during the reaction of the dihalogen monoxide and the monometal cyanurate in equations (4) and (5) above. The water formed may be advantageously employed to produce a hydrate of the desired monometal dihaloisocyanurate. For example, as shown in equation (4), when anhydrous monosodium cyanurate is reacted with the dihalogen monoxide, the monosodium dihaloisocyanurate monohydrate is formed. When monosodium monohydrate is used as a starting material, the product is monosodium dihaloisocyanurate dihydrate. Where the monometal dihaloisocyanurate produced is desired as the anhydrous salt, the by-product water formed may be removed by vaporizing the water through suitably controlling the reaction temperature and the gas flow rate through the reactor.

In the reaction using monocalcium dicyanurate as shown in equation (5), the product recovered may be treated with further water to form monocalcium dichloroisocyanurate tetrahydrate or hexahydrate.

During the reaction, it may be desirable to agitate the monometal cyanurate by mechanical means or to employ a rotating reactor having means such as flights to cascade the cyanurate. In a preferred embodiment, the process is conducted in a fluidized bed reactor where the gaseous mixture can be used advantageously to fluidize the monometal cyanurate. The principles in practice of employing fluidized bed reactors are well known as described, for example, in the Chemical Engineers Handbook, edited by R. H. Perry and C. H. Chilton, fifth edition, McGraw-Hill, 1973, section 20, pages 64–74.

The alkali metal and alkaline earth metal dihaloisocyanurates produced by the process of the present invention are recovered as dry or slightly moist products which can be used directly with no further processing required except, if desired, additional drying.

The process of the present invention is further illustrated by the following example. All percentages are by weight unless otherwise specified.

EXAMPLE

Monosodium cyanurate monohydrate (10 parts) was placed in a reaction vessel. Dichlorine monoxide was generated by feeding dry chlorine gas (25 ccs. per min.) to a reactor containing a mixture of dried yellow mercuric oxide and glass beads. Nitrogen gas (100 ccs. per min.) was added to the dichlorine monoxide and the gaseous mixture fed to the reaction vessel. The solids in the reaction vessel were agitated periodically. The reaction was conducted for about 3 hours at ambient temperature. The contact time between the dichlorine monoxide and monosodium cyanurate monohydrate was about 0.5 minutes. A dry free-flowing product was identified by infrared spectrum analysis as sodium dichloroisocyanurate dihydrate having an available chlorine content of 45.3 percent and containing some unreacted monosodium cyanurate monohydrate. The conversion of monosodium monohydrate to monosodium dichloroisocyanurate dihydrate was about 82 percent.

What is claimed is:

1. A process for producing a dihaloisocyanuric acid salt which comprises reacting a gaseous mixture containing a dihalogen monoxide and an inert gas with a solid monometal cyanurate selected from the group consisting of a monoalkali metal cyanurate, or a monoalkaline earth metal dicyanurate, said gaseous mixture being comprised of from about 1 percent to about 30 percent by volume of said dihalogen monoxide, and recovering said dihaloisocyanuric acid salt produced thereby.

2. The process of claim 1 wherein said dihalogen monoxide is selected from the group consisting of dichlorine monoxide and dibromine monoxide, and mixtures thereof, and said inert gas is selected from the group consisting of air, nitrogen, carbon dioxide, chlorine and nitrous oxide.

3. The process of claim 2 wherein a reaction temperature of from about 0° to about 175° C. is employed, and said gaseous mixture comprises from about 5 percent to about 25 percent by volume of said dihalogen monoxide.

4. The process of claim 3 wherein said dihalogen monoxide is dichlorine monoxide.

5. The process of claim 4 wherein said monoalkaline earth metal dicyanurate is selected from the group consisting of monomagnesium dicyanurate, monocalcium dicyanurate, monostrontium dicyanurate, and monobarium dicyanurate, their hydrates and mixtures thereof, and the molar ratio of said dichlorine monoxide to said monoalkaline earth metal dicyanurate is from about 1.2:1 to about 4:1.

6. The process of claim 4 wherein said monoalkaline earth metal dicyanurate is selected from the group consisting of magnesium dicyanurate, calcium dicyanurate, their hydrates and mixtures thereof.

7. The process of claim 4 wherein said monoalkali metal cyanurate is selected from the group consisting of monolithium cyanurate, monosodium cyanurate, monopotassium cyanurate, and monorubidium cyanurate, and monocesium cyanurate, their hydrates, and mixtures thereof, and the mole ratio of said dihalogen monoxide to said monoalkali metal cyanurate is from about 0.6:1 to about 2:1.

8. The process of claim 6 wherein the temperature of said reaction is from about 20° to about 100° C.

9. The process of claim 7 wherein said monoalkali metal cyanurates are selected from the group consisting of sodium cyanurate, potassium cyanurate, their hydrates, and mixtures thereof.

10. The process of claim 9 wherein said monoalkali metal cyanurate is selected from the group consisting of monosodium cyanurate, monosodium cyanurate monohydrate and mixtures thereof.

11. The process of claim 10 wherein said molar ratio of said dichlorine monoxide to said monoalkali metal cyanurate is from about 0.8:1 to about 1.2:1.

12. The process of claim 11 wherein said time of said reaction is from about 0.5 seconds to about 4 minutes.

* * * * *